United States Patent
Walston et al.

(10) Patent No.: US 7,371,218 B2
(45) Date of Patent: May 13, 2008

(54) IMMERSIVE PORTABLE ULTRASOUND SYSTEM AND METHOD

(75) Inventors: Andrew L. Walston, Seattle, WA (US); Dean J. Bidwell, Everett, WA (US); Stephen B. Hooper, Seattle, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 10/341,871

(22) Filed: Jan. 14, 2003

(65) Prior Publication Data

US 2003/0139671 A1 Jul. 24, 2003

Related U.S. Application Data

(60) Provisional application No. 60/349,949, filed on Jan. 17, 2002.

(51) Int. Cl.
*A61B 8/00* (2006.01)
(52) U.S. Cl. .................... 600/437; 600/440
(58) Field of Classification Search ........ 600/437–471; 128/915–916; 356/908; 367/7, 901
See application file for complete search history.

(56) References Cited

U.S. PATENT DOCUMENTS

| | | | | |
|---|---|---|---|---|
| 3,784,805 A | * | 1/1974 | Rolle | 367/11 |
| 3,964,296 A | * | 6/1976 | Matzuk | 73/607 |
| 4,246,792 A | * | 1/1981 | Matzuk | 73/620 |
| 5,261,404 A | * | 11/1993 | Mick et al. | 600/425 |
| 5,293,351 A | * | 3/1994 | Noponen | 367/7 |
| 5,548,564 A | | 8/1996 | Smith | |
| 5,579,768 A | | 12/1996 | Klesenski | |
| 5,590,658 A | | 1/1997 | Chiang et al. | |
| 5,690,114 A | | 11/1997 | Chiang et al. | |
| 5,722,412 A | | 3/1998 | Pflugrath et al. | |
| 5,817,024 A | | 10/1998 | Ogle et al. | |
| 5,839,442 A | | 11/1998 | Chiang et al. | |
| 5,945,770 A | | 8/1999 | Hanafy | |
| 5,957,846 A | | 9/1999 | Chiang et al. | |
| 5,957,851 A | | 9/1999 | Hossack | |
| 5,964,709 A | | 10/1999 | Chiang et al. | |
| 6,106,472 A | | 8/2000 | Chiang et al. | |

(Continued)

OTHER PUBLICATIONS

"Head-up Display Can Be Built Into Eyeglasses," by David Lieberman, EE Times, The Industry Source For Engineers & Technical Managers Worldwide; eetimes.com/story/OEG19990420S0009; Apr. 20, 1999.

(Continued)

*Primary Examiner*—Francis J. Jaworski

(57) ABSTRACT

A portable ultrasound system provides immersive viewing of images. A small, lightweight scope includes a transducer and a display. The display is adapted for viewing ultrasound images close to the eye of the user, such as within five inches or a couple feet of the eye. By adapting the system for close viewing, the ultrasound system is sensory immersive, such as an otoscope or endoscope. A magnifying lens is positioned adjacent to a display screen. The magnifying lens adapts the small display screen for viewing close to the user's eye. A shade or eyepiece extends away from and at least partly around the display screen. The shade allows viewing in many different lighting conditions. Alternatively, the ultrasound image is viewed on a head mounted display attached to glasses or a helmet.

8 Claims, 3 Drawing Sheets

U.S. PATENT DOCUMENTS

| | | | |
|---|---|---|---|
| 6,113,547 A | 9/2000 | Catallo et al. | |
| 6,117,085 A | 9/2000 | Picatti et al. | |
| 6,121,718 A | 9/2000 | Mohr, III | |
| 6,135,961 A | 10/2000 | Pflugrath et al. | |
| 6,139,496 A * | 10/2000 | Chen et al. | 600/437 |
| 6,142,946 A | 11/2000 | Hwang et al. | |
| 6,181,644 B1 * | 1/2001 | Gallagher | 367/131 |
| 6,251,073 B1 | 6/2001 | Imran et al. | |
| 6,256,529 B1 * | 7/2001 | Holupka et al. | 600/427 |
| 6,383,139 B1 | 5/2002 | Hwang et al. | |
| 6,398,733 B1 | 6/2002 | Simopoulos et al. | |
| 6,416,475 B1 | 7/2002 | Hwang et al. | |
| 6,429,574 B1 | 8/2002 | Mohr, III et al. | |
| 6,471,651 B1 | 10/2002 | Hwang et al. | |
| 6,475,146 B1 | 11/2002 | Frelburger et al. | |
| 6,530,887 B1 | 3/2003 | Gilbert et al. | 600/459 |
| 6,540,685 B1 * | 4/2003 | Rhoads et al. | 600/459 |
| 6,575,908 B2 * | 6/2003 | Barnes et al. | 600/443 |
| 6,746,402 B2 * | 6/2004 | Ustuner | 600/462 |
| 6,875,178 B2 | 4/2005 | Phelps et al. | |

OTHER PUBLICATIONS

"NCO Helps Create New Ultrasound Technology," by 2nd Lt. Nathan Broshear 82nd Training Wing Public Affairs; Public Affairs (AETC News Service); Jul. 10, 2002.

MicroOptical—Making Portable Practical; www.microopticalcorp.com/applications.html; date unknown (printed Nov. 11, 2002.

* cited by examiner

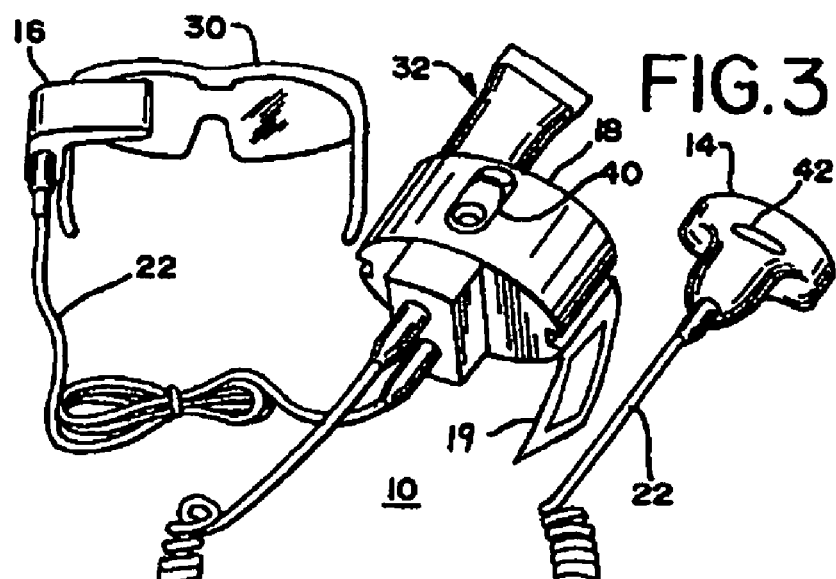
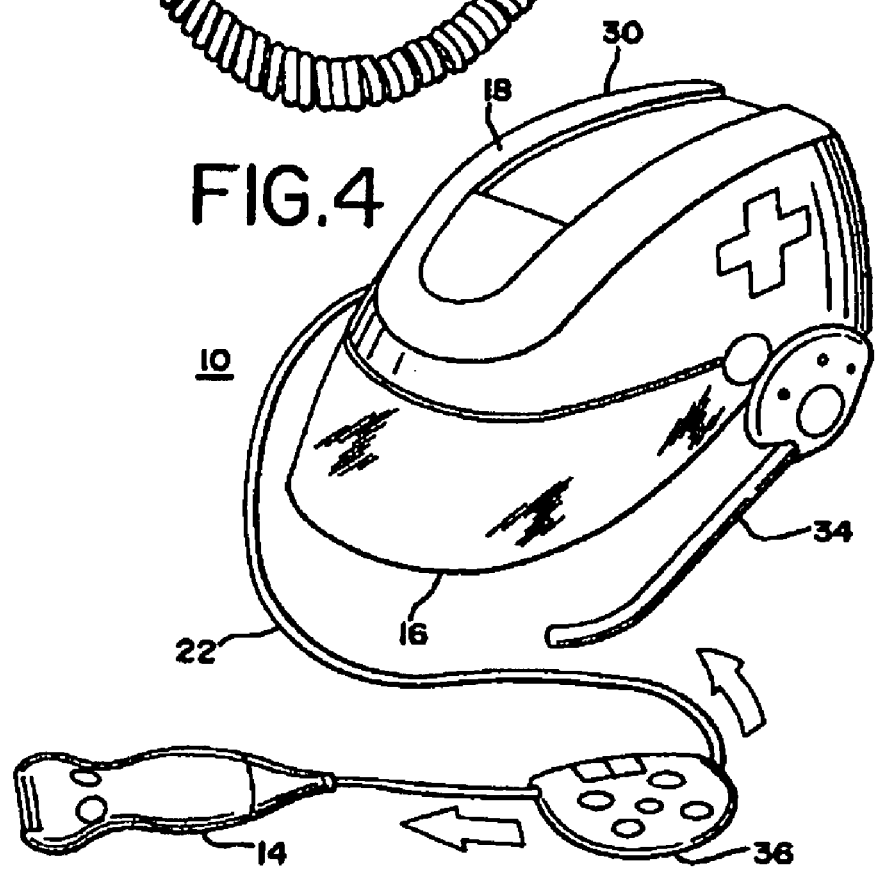

IMMERSIVE PORTABLE ULTRASOUND SYSTEM AND METHOD

RELATED APPLICATIONS

This application claims the benefit of the filing date pursuant to 35 U.S.C. §119(e) of Provisional Application Ser. Nos. 60/349,949 (Medical Hand-held Device), filed Jan. 17, 2002, the disclosure of which is incorporated herein by reference.

BACKGROUND

The present invention relates to portable diagnostic ultrasound systems. In particular, a hand-held ultrasound system is provided.

Conventional ultrasound imaging systems typically include a hand-held transducer probe coupled by a cable to a large processing and display workstation. The transducer probe includes an array of ultrasonic transducers which transmnit and receive ultrasonic energy for imaging a patient. The received ultrasonic energy is converted to electric signals by the transducer and passed to the workstation. The workstation detects, filters and otherwise processes the information to generate a two- or three-dimensional representation of the scanned region. Limited mobility is provided by such systems. Typically, the ultrasound system is maintained in a specific location and patients are brought to the ultrasound system.

A more portable ultrasound system is disclosed in U.S. Pat. No. 6,312,381, the disclosure of which is incorporated herein by reference. The system shown in FIG. 11 of the '381 patent is designed to be carried by a single person, such as weighing less than 30 pounds. The system includes a large screen and full-size or close to full-size keyboard. The system is carried as a briefcase or package.

Additional portability is provided by one or more of the systems disclosed in U.S. Pat. Nos. 5,957,846, 6,251,073, 5,817,024 and 6,383,139, the disclosures of which are incorporated herein by reference. Different amounts of portability are provided. For example, one system includes a hand-held scan head coupled by a cable to a portable data processor and display unit, such as a laptop computer. Other systems include separate hand-held components including a small display screen and transducer components. In yet other embodiments, a small display screen connects with a transducer in a hand-held embodiment. FIG. 38 of the U.S. Pat. No. 5,957,846 shows a transducer 704 connected as a stethoscope to two speakers or audio transmitting tubes for insertion within the ears. A separate cord connects to a flat-panel display and user interface, such as a keypad or mouse control. However, these portable hand-held devices may perform poorly in unregulated environments, such as outside of a temperature and lighting controlled room.

BRIEF SUMMARY

The present invention is defined by the following claims or later added claims supported by any disclosure herein, and nothing in this section should be taken as a limitation on those claims. By way of introduction, the preferred embodiments described below include a portable ultrasound system and method for immersive viewing of ultrasound information. A small, lightweight scope includes a transducer and a display. The display is adapted for viewing ultrasound images close to the eye of the user, such as within five inches or a couple feet of the eye. By adapting the system for close viewing, the ultrasound system is sensory immersive, such as an otoscope or endoscope.

In one aspect, a magnifying lens is positioned adjacent to a display screen. The magnifying lens adapts the small display screen for viewing close to the user's eye. In another aspect, a shade or eyepiece extends away from and at least partly around the display screen. The shade allows viewing in many different lighting conditions. In yet another aspect, the ultrasound image is viewed on a head mounted display attached to glasses or a helmet. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 is a graphical representation of an alternative embodiment of an ultrasound system for immersive viewing.

FIG. 4 is yet another alternative embodiment of a portable ultrasound system for immersive viewing.

DETAILED DESCRIPTION OF THE PREFERRED EMBODIMENTS

Configuring a portable ultrasound system as a scope emulates peaking into the body for a look. A scope is a sensory immersive device, blocking ambient distractions and focusing a user's attention to the imaging task at hand. Similar experiences are provided in other medical diagnostic devices, such as otoscopes and endoscopes. Sensory immersive scopes can be used in various lighting conditions. A miniature display device and ultrasound imaging electronics and transducer are provided in a compact configuration. The portability combined with immersive viewing techniques allows use in various applications, such as by a doctor making rounds or a paramedic at any of various incident scenes, increasing the standard of care. Portability allows the ultrasound system to be worn around the neck or otherwise easily carried, providing a simple device that encourages quick and easy ultrasound examinations.

Figure 1:
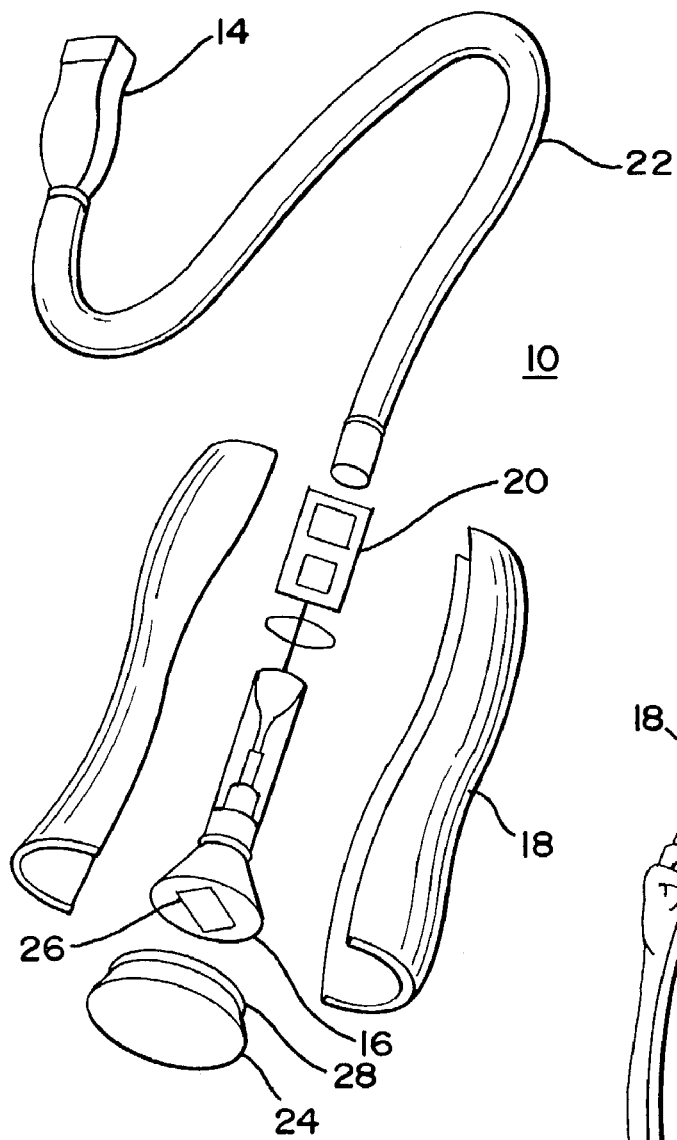
FIG. 1 is an exploded view of a portable hand-held ultrasound system of one embodiment.
Figure 2:
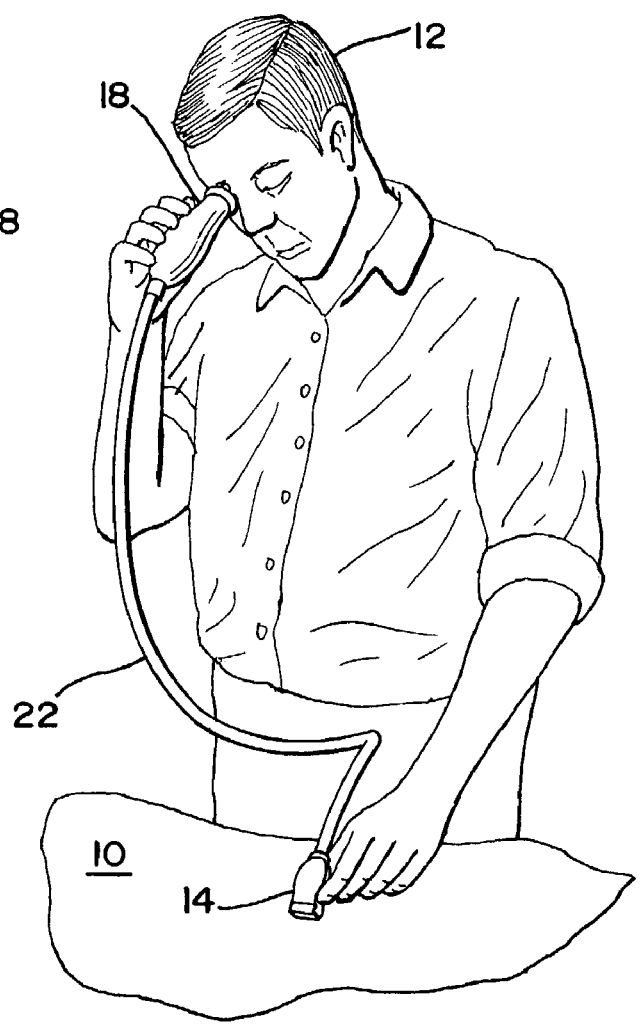
FIG. 2 is a graphical representation of the use of the ultrasound system of FIG. 1.

A portable ultrasound system for immersive viewing of ultrasound information is shown in FIGS. 1 and 2. FIG. 1 shows an exploded view of the portable ultrasound system 10 of one embodiment, and FIG. 2 shows the portable ultrasound system 10 being operated by a user 12, such as a doctor, paramedic, or other person interested in internal ultrasound examination of a patient. Other embodiments with different or similar shapes and sizes may be used. The portable ultrasound system 10 includes a transducer 14, a display 16, a housing 18, ultrasound circuitry 20 and a cord 22. Additional, different or fewer components may be provided, such as providing for wireless transmission between the transducer 14 and the display 16 or providing a shade 24 for the display 16. In one embodiment, the system 10 comprises components described in U.S. Pat. No. 6,780,154.

The transducer 14 comprises an array of elements for transducing between acoustical and electrical energies, such as a one-dimensional, two-dimensional or single element transducer. Any of a phased array, linear array, curved array or other arrays may be used. The elements are surrounded by a housing designed for holding by the user 12. For example, the housing of the transducer 14 includes a grip or other oblong, rounded or cubed structures for ease of holding by a user while placing a window on the housing associated with the array adjacent to a patient. In one embodiment, the transducer 14 is sized to be small for portability, such as using more closely-spaced elements adapted for higher ultrasound frequencies or using fewer elements within the array. In alternative embodiments, the transducer 14 is larger, such as being sized to be generally similar to the size of the housing 18 or larger. The weight is also similar but may be less or more. Any of various transducers 14 now known or later developed may be used, such as a cardiac transducer.

The transducer 14 may be free of further electronics or include additional electronics, such as preamplifiers and/or portions of transmit and receive beam forming circuitry. For example, the transducer 14 includes time division multiplexing circuitry, such as disclosed in U.S. Pat. No. 6,875,178, filed Jun. 27, 2002, the disclosure of which is incorporated herein by reference. A multiplexer, amplifiers and optional time gain controls are provided for multiplexing receive channels onto a single or fewer number of cables within the cable 22 than elements within the transducer 14. In other embodiments, additional ultrasound circuitry, such as the ultrasound circuitry 20 for detecting and scan converting are provided in the transducer 14.

In one embodiment, the transducer 14 is releasably connectable with the housing 18 and the ultrasound circuitry 20. For example, an electrical and physical connector is provided between the cable 22 and the transducer 14 or between the cable 22 and the housing 18. The connector allows for electrical and physical connection of miniaturized coaxial cables or other electrical conductors. The releasable connection allows for different transducers 14 to be connected with the housing 18. In alternative embodiments, the connection between the transducer 14 and the housing 18 is set or otherwise permanent.

The display 16 is adapted for viewing ultrasound images within five inches of the eye of the user 12. The display 16 comprises a miniature CRT, miniature LCD, a view finder (e.g., electronic displays used on camcorders or other devices to be positioned close to the eye), or other now known or later developed display devices. The display 16 provides any of various resolutions, such as 320×240 pixels, lower or higher resolutions. In one embodiment, the display outputs black and white information, but a color display may be used. The display 16 connects with the ultrasound transducer 14 for displaying ultrasound images.

One or combinations of various structures adapt the display 16 for use within five inches or closer to the eye of the user 12. In one embodiment, the size of the display screen 26 is sufficiently small to encourage placement close to the user's eye. For example, the display area of the display 16 is less than four square inches (e.g., the display area is one square inch or less).

In another embodiment, a magnifying lens 28 is positioned adjacent to the display screen 26 of the display 16. The magnifying lens 28 magnifies to the extent desired for increasing the perceived size of the display close to the eye of the user 12. The magnification may be adapted for greater or lesser distances, such as a foot or more (e.g. arms length).

In another embodiment, the display 16 is adapted for use close to the eye by including a shade 24 extending away from and at least partly around the display screen 26. For example, an eyepiece of rubber, foam, plastic, metal or other material adapting for placement against the skin and/or to shade light from the display screen 26 when held away from the skin. The shade 24 extends completely around or encircles the display screen 26 in one embodiment, but may extend only partly around and vary in the amount of extension away from the display screen 26 as a function of placement along the circumference of the display screen 26: The shade 24 blocks light from the display screen 26 or magnifying lens 28, avoiding glare and allowing immersive use in various lighting conditions.

By adapting the display 16 for use close to the user's eye, a scope. configuration that blocks out visual distractions and can be used in various lighting conditions is provided. Unwanted glare, contrast shifts, viewing angle limitations and increased size is avoided as compared to flat panel displays (e.g., LCD displays of four square inches or more). The sensory immersive scope configuration focuses the user's attention on the ultrasound image on the display 16.

Figure 8:
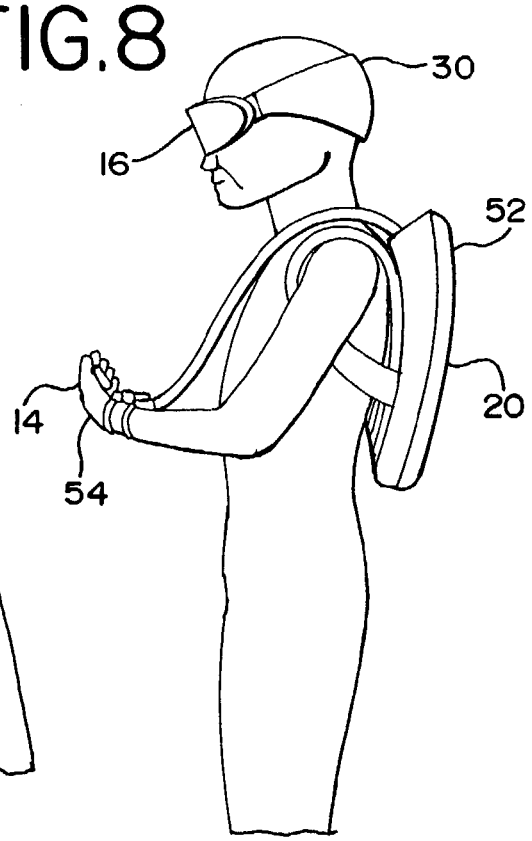
FIG. 8 is a alternative embodiment of a portable ultrasound system for immersive viewing.

FIGS. 3, 4 and 8 show yet another embodiment of the portable ultrasound system 10 with a display 16 adapted for use within five or less inches of the user's eye. The display 16 includes a head mount 30. In the embodiment of FIG. 3, the head mount 30 comprises glasses (e.g., glasses acting as a visor) with ear pieces or straps for holding the glasses 30 to the user's head. In the embodiment of FIG. 4, the head mount 30 is a helmet that optionally includes the ultrasound circuitry 20. The display 16 comprises one or more of an LCD panel with a prism for projecting an image onto the eye glasses or visor of the display 16, a laser or other device for projecting the image directly onto the eye of the user 12, a reflective surface for reflecting an image on a semitransparent or opaque screen or surface, a view finder (e.g., a miniature television, a miniature CRT, or miniature LCD screen), or other now known or later developed displays for use on head mounted devices. The display 16 using a head mount 30 allows for a free hand to place needles, apply gel or perform other tasks while scanning.

In the embodiment of FIG. 3, the housing 18 is adapted for hanging on a belt, on a shoulder strap or otherwise being held adjacent to the user 12. The belt adaptation may allow use of a larger battery and additional controls. The housing 18 as shown is adapted for holding the transducer 14 when not in use and a tube of gel 32. Other housings with fewer, different or additional adaptations may be provided. The housing 18 also allows for releasable connection of the display 16 and the transducer 14 by unplugging the cords 22 from the housing 18, but more permanent connections may be provided.

In the embodiment of FIG. 4, the helmet or head mount 30 includes the ultrasound electronics 20 and a microphone 34 for voice recognition functions. An audio or speaker system and other functions may be provided on the helmet 30. The visor for the display 16 is mounted to the helmet by hinges, allowing rotation away from the user 12 when not in use. By providing a visor that is semitransparent, the user 12 may focus on the display 16 or beyond the display 16. The optional voice recognition system using the microphone 34 may control the basic functions of the ultrasound system 10. Alternatively or additionally, a control pad 36 can be fixedly or adjustably placed along the length of the transducer cable 22. Using infrared, radio frequency, wired or other connections, the controller 36 communicates with the ultrasound electronics in the helmet 30. The audio system allows the user 12 to listen to audio Doppler information and may be used as a standard communications device. A built-in light may be provided for use in dimly lit areas.

In the embodiment of FIG. 8, the head mount 30 comprises a band with a visor for the display 16. The ultrasound electronics 20 are provided in a back pack 52, but may alternatively be located in the head mount 30 or the transducer 14. A control pad 36 is provided with the transducer 14 on a glove or wrist mount 54, but may be provided separately.

Figure 5:
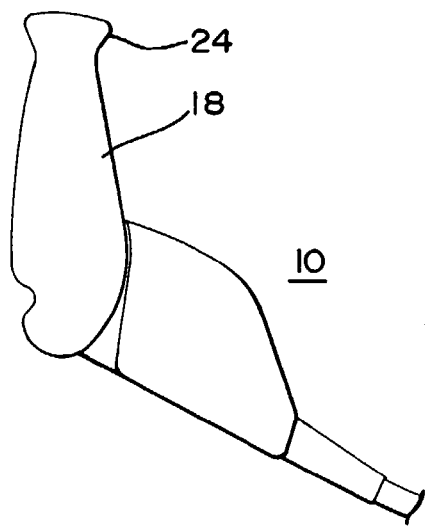
FIG. 5 is a side view of yet another embodiment of a portable ultrasound system for immersive viewing.

The housing 18 comprises plastic, rubber, metal, other materials now known or later developed, or combinations thereof. The housing 18 connects with the display 16, such in a clam shell embodiment or a formed or injection molded housing with a panel or aperture for insertion or access to the display 16 and electronics 20. In one embodiment shown in FIGS. 1 and 2, the housing is shaped for ergonomic use or holding by the user 12. In other embodiments, different shapes are used, such as a belt or shoulder strap attachment housing 18 shown in FIG. 3. For portability, the housing 18 is less than 12, less than eight or less than six inches in any dimension. For example, the housing 18 of FIGS. 1 and 2 is about six inches long and has a generally round circumference sized to fit within a user's hand. The shape provides a portable scope for immersive viewing. Other shapes adapted to be held by a user's hand may be used. For example, FIG. 5 shows a rotatable microscope configuration. In this embodiment, the shade 24 is formed as part of the housing 18 rather than the separate component as shown in FIG. 1. The housing 18 is bifurcated to allow one piece of the housing 18 with the display 16 to rotate relative to another piece of the housing 18. The hinge may allow the housing 18 to fold together to a more compact size or more convenient position for portability. Similar to a microscope, the user holds the housing 18 and rotates the portion of the housing 18 to place adjacent to or close to the eye of the user 12.

In yet another alternative embodiment, an additional flip-out display 19 connects with the housing 18, to facilitate sharing the ultrasound image with other users. The flip-out display 19 is larger than the display 16 or display screen 26. In one embodiment, the flip-out display 19 comprises a LCD or other flat panel display, such as used on video recorders or other consumer goods for comfortable use at arm's length or similar distances from the eye of the user 12. The flip-out display 19 is used in controlling lighting environments with minimal glare. For more adverse lighting environments, the user uses the display 16. The flip-out display 19 is rotatably or extendably connected to the housing 18.

In yet another alternative embodiment, the housing 18 is configured as binoculars or a housing with two displays 16. The additional display 16 is positioned for placement in front of one of the user's eyes while the other display is positioned in front of the other of the user's eyes. A fixed distance may be provided between the two displays 16 or a hinged or expandable connection may be provided for allowing increases or decreases in the separation between the two displays 16. The binocular configuration allows for a more completely immersive viewing of ultrasound images.

The ultrasound circuitry 20 within the housing 18 may output two of the same or two different two-dimensional images, one to each of the displays 16. Using different images, a three-dimensional viewing or stereoscopic view is provided by the system 10. Portable three-dimensional imaging may be provided using the binocular configuration.

Figure 6:
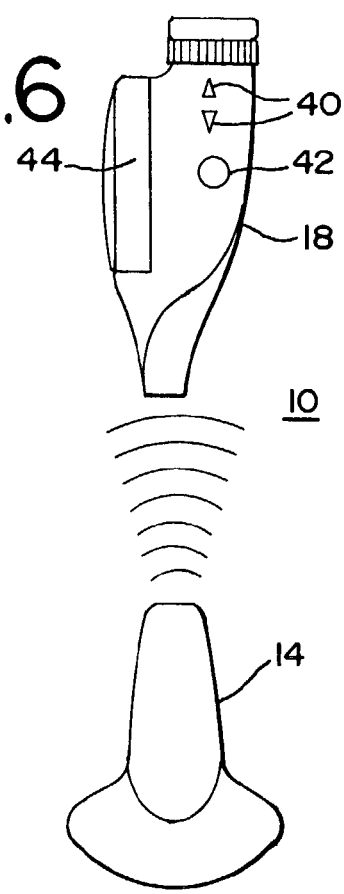
FIG. 6 is an embodiment of a portable ultrasound system for immersive viewing using wireless connection between two components.

Any one of various sources of power may be provided for operating the portable ultrasound system 10. As shown in FIG. 6, a battery 44 connects to or within the housing 18 and electrically connects to the ultrasound circuitry 20. As an alternative to a battery 44, a plug or cord may be provided for accessing power from another source. Transmitted power, such as microwaves, may also be provided.

Buttons 40, 42 allow control of the portable ultrasound system 10. The buttons 40, 42 comprise rocker switches, single buttons, multiple buttons, membrane buttons, capacitive sensing buttons, menu selection buttons, toggle switches or other devices now known or later developed for inputting information. Additional user inputs may be provided, such as a track ball, joystick, scroll wheel, or other device. In one embodiment shown in FIGS. 3 and 6, a rocker switch 40 is provided for increasing or decreasing the depth of an ultrasound scan, and/or increasing or decreasing another function (e.g., overall gain). An on/off or start and stop scan button 42 is also provided. By minimizing the number of user inputs, such as providing a single rocker switch 40 and the on/off button 42, a more simple user friendly device is provided. In alternative embodiments, additional inputs are provided for additional control functions, such as any of various control functions provided on other portable or larger ultrasound systems. In one embodiment, a menu selection input device is provided for selecting control of various functions through software menu selection. Where a gain control input is not provided, a software gain or set gain control function may be provided, such as disclosed in U.S. Pat. Nos. 5,579,768 and 6,398,733, the disclosures of which are incorporated herein by reference.

As shown in FIG. 6, the various user inputs or buttons 40, 42 are provided on the housing 18. By providing the user inputs on the housing 18, incidental adjustment or changes in the scanning due to movement by the user of the transducer 14 are avoided. In alternative embodiments, one or more of the buttons are provided on the transducer 14, such as shown in the embodiment of FIG. 3. In yet other alternative embodiments, all the user inputs are provided on the transducer 14. A separate user input device may be provided, such as the user input module 36 shown in FIG. 4 or a user input module connected to the housing 18 by a wire or wirelessly. A microphone and associated processor may be provided for voice activation or control of the portable ultrasound system 10 as an alternative or additional source of user input.

The ultrasound circuitry 20 connects with the display 16 within the housing 18. The ultrasound circuitry 20 comprises one or more of a digital signal processor, application specified integrated circuit, general processor, analog device, digital device, detector, transmit beam former, receive beam former, scan converter, filter, memory, buffer, data bus, analog devices now known or later developed, digital devices now known or later developed, and combinations thereof. Any of the various ultrasound circuitry and associated software described in the patents cited herein may be used. In one simple form, the ultrasound circuitry 20 includes a transmit beamformer for generating scan lines in a single format to one of various user selectable depths, a receive beamformer for receiving along the scan lines, a B-mode detector, a scan converter for converting from the scan format to a display format, one or more optional filters, and one or more control processors responsive to the user input. In alternative embodiments, different additional or fewer devices are provided, such as substituting the B-mode detector with a Doppler detector. In more complex embodiments, additional ultrasound functionality is provided, such as including functions and associated hardware from now known or later developed portable or larger ultrasound systems. For example, color flow, three-dimensional processing, selection of different transducers and associate scan formats, different filtering, harmonic receiving, providing different processes for different types of examination or applications, or other additional functionality and associated hardware. In one embodiment, audio Doppler processing is also incorporated in output to one or more speakers or earphones.

As shown, the ultrasound circuitry 20 is positioned within the housing 18 and electronically communicates with the transducer 14 through the cable 22 and the display 16. In alternative embodiments, part or all of the ultrasound circuitry 20 is included within the transducer 14. In alternative embodiments, the ultrasound circuitry 20 is distributed amongst three or more components, such as shown in FIG. 3 with ultrasound circuitry in the transducer 14, housing 18 and in the display 16.

To reduce power requirements for transmission of ultrasound imaging, parallel beam forming where two or more transmit or receive beams are generated simultaneously may be used. Maximum information beam forming may be provided where a plane wave is transmitted and the information received at each receive element is stored in one or more memories for forming a plurality of different receive beams. Phase and amplitude signal processing using reduced power requirements may also be used. By shortening the signal acquisition time, few transmit and receive events are needed to achieve desired frame rates for a handheld application. Frame rates are the same or less than associated with larger ultrasound systems. While not in use, the analog portions of the transmit and receive circuitry are unpowered or disconnected to save power, such as turning off the analog components about 85% of the time during scanning. Other electronics may be disabled when not in use to conserve power. By limiting the time of actual transmit and receive events relative to the time beam and imaging forming, and temporally interleaving the two, noise is temporally isolated between the transmit and receive functions.

One or more dedicated transmit elements positioned adjacent to dedicated receive elements may be used in the transducer 14. By positioning transmit elements on each side of a receive array, the transmitters are capable of generating ultrasound pressure appearing to emanate from a single point in space. To keep the power supply as simple and as small as possible, the number of different power forms or voltages required within the portable ultrasound system 10 is reduced or kept at a minimum, such as one voltage provided for transmit and receive analog functions and a second voltage provided for analog to digital conversion and digital signal processing. To avoid a high voltage supply, a step-up transformer and convention PZT elements are used, a multilayer PZT is used or combinations thereof. Where multilayer PZT is used, a transmitter, in one embodiment, communicates between the transducer 14 and the housing 18 to avoid large losses in the cable 22, but a cable 22 may be used. By using FET devices with very low or ultra low resistance (e.g., 20 milliohms), a very compact transmit and receive cell runs on a 5 volt power supply. Two transistors drive the elements during a transmit cycle and a transmit and receive switch is formed by two other transistors for isolating the receive circuitry. In alternative embodiments, a split power supply with positive and negative voltages may achieve higher acoustic power and wider received dynamic range. Any of various reduced power requirement transmitters or receivers and associated circuitry may be used.

The transducer 14 electrically and physically connects with the housing 18 and the display 16 through one or more of the cords 22. The cord 22 comprises one or more coaxial cables, such as miniaturized coaxial cables, wrapped in a rubber or plastic protective sheath. In alternative embodiments, wires of copper or other conducting material are used. Separate electrical connections may be provided within the same or separate cables 22 for each element of the transducer 14 to the ultrasound circuitry 20, but multiplexing may be used to minimize the number of cables extending from the transducer 14 to the housing 18 or ultrasound circuitry 20. In the embodiment shown in FIG. 3, the cable 22 extending from the transducer 14 to the housing 18 includes a plurality of miniaturized coaxial cables or other now known or later developed electrical conductors for transmitting received ultrasound signals. The cable 22 extending from the housing 18 to the display 16 comprises one or more electrical conductors for transmitting video signals. Where the cables 22 interconnect the various components of the portable ultrasound system 10, no wireless communications, transmissions or associated electronics are used, further reducing the size of the portable ultrasound system 10 and the drain on any power source.

As an alternative to connection with the cable 22, a radio frequency, infrared or other wireless connection us provided as shown in FIG. 6. The transducer 14 includes a transmitter, a receiver and/or a transceiver. Data from one or more elements of the transducer 14 is multiplexed using any of various communications formats, such as time or frequency multiplexing schemes now known or later developed or an ultra wide band frequency format. The transmitter transmits using broadcast video standards through video encoding or RF carrier modulation. The RF transmission is optimized for any various distances, such as around two meters of range. Multiple directional infrared receivers, directional infrared transmitters and receivers, infrared or radio frequency control or feedback for control of automatic selection of the transmit frequency or receive antennas may be used to reduce the transmit power required. Analog or digital radio frequency transmissions may be used, such as a digital communication link with 0.1 to 2 megabits per second in an uncompressed or compressed format in a low power transmission. A battery or other power sources in the transducer 14 operate the electronics within the transducer 14.

In response to an initiation signal either transmitted wirelessly to the transducer 14 or input on a input device on the transducer 14, the transducer 14 generates received ultrasound data and transmits the data to the housing 18 or ultrasound electronics 20. A receiver and associated antenna on or within the housing 18 with or separate from the ultrasound electronics 20 receives the transmitted data. The receiver formats the data for processing by the ultrasound electronics. The receiver is connected with the display 16 through the ultrasound electronics 20, such as a direct circuit board connection, through a cord, or through another wireless link. A transmitter or transceiver may also be provided in the housing 18 for controlling transmissions by the transmitter in the transducer 14 and providing control instructions to the transducer 14. Alternatively, a one-way wireless link is provided from the transducer 14 to the housing 18. Signals embedded in the one-way transmission or user inputs are used to activate appropriate functions.

The portable ultrasound system 10 is adapted for quick and efficient ultrasound scanning in various environments. No or minimal outputs are provided. In alternative embodiments, one or more of a variety of outputs for archiving or transferring images to other devices is provided. For example, a video output connects with a heads up display, a video recorder, additional monitors or flat panel screens. An audio output or connector may also be provided. As another example, a USB or other computer-related output is provided for transferring image data for viewing or archiving on a hard drive, CD ROM or other memory device. Any other outputs now known or later developed may be used. One or more outputs are used for communicating information from the portable ultrasound system 10 to other individuals, such as other medical technicians near the patient being scanned or remote from the patient being scanned. The outputs are output in real time with the scan or may be later output where a memory for storing one or more images is provided as part of the portable ultrasound system 10.

In an alternative embodiment, a transmitter connects with the ultrasound circuitry 20, and a receiver is spaced apart from the transducer 14 and the ultrasound circuitry 20. The receiver is operable to receive ultrasound data from the transmitter for archiving or display on devices separate from the portable ultrasound system 10. The wireless connection to memory or viewing devices allows for unencumbered scanning while providing ultrasound images to people other than the user for diagnosis. Any of the various transmitter and receiver circuits discussed above, now known or later developed may be used, including transceiver technologies in any of time or frequency multiplexing formats.

FIG. 2 shows a method for viewing ultrasound images with the portable ultrasound system 10. The user 12 holds the ultrasound transducer 14 adjacent to a patient with one hand. The housing 18 with the display 16 is held in the other hand of the user. In one embodiment, the display of the housing 18 is placed within five inches or less of an eye of the user. As shown in FIG. 2, an eye piece or shade 24 of the housing may be placed adjacent to the skin around the eye, but may be alternatively held slightly away from the user's face. In yet other alternative embodiments, the housing 18 and the associated display 16 are held greater than five inches away from the eye of the user, such as one to two feet. Whether adjacent the eye or spaced from the user's eye, the shade 24 extending at least partly around and extending from the small display screen prevents glare, allowing the user 12 to view images on the viewfinder or display screen in various lighting conditions. In the embodiment shown in FIGS. 3 and 4, the display is positioned near the eye by placing the head mount on the user's head, and lowering or moving the display or associated visor as appropriate.

Figure 7:
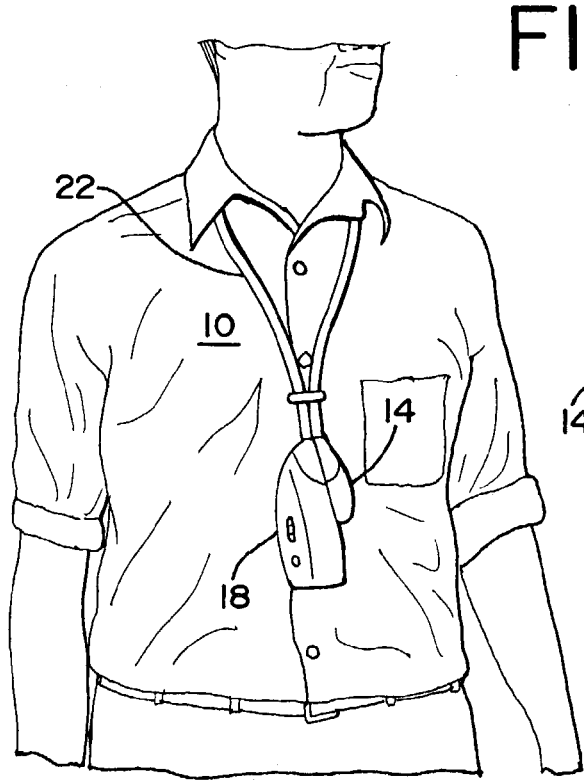
FIG. 7 is a graphical representation of a convenient method of storing the portable ultrasound system of FIG. 1 between uses.

The portable ultrasound system 10 is easily carried in a pocket, attached to the belt with a clip or worn around the neck of the user 12 similar to a stethoscope as shown in FIG. 7. The cord 22 is draped around the user's neck. The transducer 14 and housing 18 are equally balanced in one embodiment. The size of the transducer 14 may be increased to provide more balanced electronic weight distribution. The equal balancing allows the portable ultrasound system 10 to remain draped around the user's neck without further clipping or attachment. In one embodiment, the portable ultrasound system 10 weighs 10-12 ounces, but heavier or lighter portable ultrasound systems 20 may be provided. In other embodiments, magnets, a cord clip, a clip on the housing 18 or on the transducer 14, an expandable loop or other connection holds the transducer 14 adjacent to the housing 18 or holds two portions of the cord 22 together. The portable ultrasound system 10 of the embodiment shown in FIG. 3 includes a clip on the housing 18 for attaching to the user's belt. Other embodiments with different shapes may be designed to be worn or carried in pouches, or shoulder straps, attached to other devices, or in any convenient manner. For example, the portable ultrasound system 10 of FIG. 6 is adapted so that both the transducer 14 and the housing 18 clip to a belt, clip to each other or may be carried in a pocket.

While the invention has been described above by reference to various embodiments, it should be understood that many changes and modifications can be made without departing from the scope of the invention. For example, any of various electronics for transmitting, receiving and signal processing of ultrasound data may be used. As another example, a variety of shapes and sizes of the housing 18 and transducer 14 may be used. It is therefore intended that the foregoing detail description be understood as an illustration of the presently preferred embodiment of the invention, and not as a definition of the invention. It is only the following claims, including all equivalents, that are intended to define the scope of the invention.

What is claimed is:

1. A portable ultrasound system for immersive viewing of medical diagnostic ultrasound information, the system comprising:
    an ultrasound transducer;
    a display operatively connected with the ultrasound transducer, the display adapted for viewing medical diagnostic ultrasound images within five inches of an eye;
    a housing connected with the display; and
    a flip-out display connected with the housing, the flip-out display larger than the display.

2. The portable ultrasound system of claim 1 wherein the display comprises a display screen and a magnifying lens positioned adjacent the display screen.

3. The portable ultrasound system of claim 1 wherein the display comprises a display screen and a shade extending away from and at least partly around the display screen.

4. The portable ultrasound system of claim 3 wherein the shade comprises an eyepiece.

5. The portable ultrasound system of claim 1 further comprising a head mount, wherein the display comprises a visor connected with the head mount the visor being rotatable to a position away from at least one eye and a position in front of the at least one eye.

6. The portable ultrasound system of claim 1 wherein the display is connected with a housing, the housing being less than eight inches in any dimension.

7. The portable ultrasound system of claim 1 wherein a cord connects the transducer with the display.

8. The portable ultrasound system of claim 1 further comprising:
    a housing connected with the display and an additional display, the housing configured as binoculars.

* * * * *